(12) United States Patent
Cobianu et al.

(10) Patent No.: US 8,372,674 B2
(45) Date of Patent: Feb. 12, 2013

(54) METHOD FOR CHEMICAL SENSOR FABRICATION AND RELATED SENSOR

(75) Inventors: Cornel Cobianu, Bucharest (RO); Bogdan-Catalin Serban, Bucharest (RO)

(73) Assignee: Honeywell International Inc., Morristown, NJ (US)

( * ) Notice: Subject to any disclaimer, the term of this patent is extended or adjusted under 35 U.S.C. 154(b) by 773 days.

(21) Appl. No.: 12/362,636

(22) Filed: Jan. 30, 2009

(65) Prior Publication Data
US 2009/0193874 A1 Aug. 6, 2009

(30) Foreign Application Priority Data
Feb. 1, 2008 (RO) ........................................ 08-0092

(51) Int. Cl.
*H01L 21/00* (2006.01)
(52) U.S. Cl. .......................................... 438/49; 73/24.06
(58) Field of Classification Search ................. 73/23.34, 73/24.01, 24.06; 438/50, 51, 52, 53
See application file for complete search history.

(56) References Cited

U.S. PATENT DOCUMENTS

| | | | | |
|---|---|---|---|---|
| 4,382,386 A * | 5/1983 | Coussot et al. | ................. | 73/703 |
| 6,852,561 B2 * | 2/2005 | Bidard et al. | .................... | 438/50 |
| 7,000,298 B2 * | 2/2006 | Cook et al. | ................... | 29/25.41 |
| 7,198,981 B2 * | 4/2007 | Avramescu et al. | ........... | 438/107 |
| 7,302,864 B2 * | 12/2007 | Liu et al. | ......................... | 73/862 |
| 7,576,470 B2 * | 8/2009 | Kumar et al. | ............ | 310/313 R |
| 7,891,252 B2 * | 2/2011 | Cobianu et al. | ................. | 73/756 |
| 7,930,923 B2 * | 4/2011 | Patel et al. | .................... | 73/23.34 |
| 2005/0231067 A1 | 10/2005 | Cook et al. | | |
| 2006/0049714 A1 * | 3/2006 | Liu et al. | .................... | 310/313 R |
| 2006/0075820 A1 | 4/2006 | Cobianu et al. | | |
| 2006/0086188 A1 | 4/2006 | Avramescu et al. | | |
| 2006/0249384 A1 * | 11/2006 | Kim et al. | ...................... | 204/424 |
| 2007/0028667 A1 * | 2/2007 | Kim et al. | ..................... | 73/23.34 |
| 2007/0114889 A1 | 5/2007 | Cobianu et al. | | |
| 2007/0126072 A1 | 6/2007 | Cobianu et al. | | |
| 2007/0164633 A1 | 7/2007 | Cobianu et al. | | |
| 2007/0164859 A1 | 7/2007 | Cobianu et al. | | |
| 2008/0156100 A1 * | 7/2008 | Hines | ............................... | 73/584 |
| 2008/0229831 A1 | 9/2008 | Serban et al. | | |
| 2008/0265711 A1 | 10/2008 | Kumar et al. | | |
| 2010/0058834 A1 * | 3/2010 | Cobianu et al. | ............. | 73/24.01 |

FOREIGN PATENT DOCUMENTS

| | | | |
|---|---|---|---|
| EP | 1830169 A1 * | 9/2007 | |
| WO | WO 2007/061831 A1 | 5/2007 | |

* cited by examiner

*Primary Examiner* — Lisa Caputo
*Assistant Examiner* — Punam Roy (57) ABSTRACT

A method includes forming a hole in a first wafer and forming a sensor structure in or on a second wafer. The second wafer includes a piezoelectric material. The method also includes bonding the first wafer and the second wafer, where the sensor structure is located between the wafers. The method further includes forming a sensing layer by depositing material between the wafers through the hole in the first wafer. The sensing layer could be formed by depositing a sensing layer material on the second wafer using direct printing. Also, the hole through the first wafer could be formed using ultrasonic milling, micro-drilling, laser drilling, wet etching, and/or plasma etching. A spacer material could be used to bond the wafers together, such as frit glass paste or an organic adhesive. Trenches could be formed in the first wafer to facilitate easier separation of multiple sensors.

20 Claims, 5 Drawing Sheets

METHOD FOR CHEMICAL SENSOR FABRICATION AND RELATED SENSOR

CROSS-REFERENCE TO RELATED APPLICATIONS

This application claims priority under 35 U.S.C. §119 to Romanian Patent Application No. a/2008-00092 filed on Feb. 1, 2008.

TECHNICAL FIELD

This disclosure relates generally to sensors and more specifically to a method for chemical sensor fabrication and related sensor.

BACKGROUND

Wireless and wired sensors can be used in a wide variety of industries and environments. For example, wired and wireless chemical sensors can be used in process control systems to detect chemical emissions or chemical concentrations and to take appropriate actions to control a process. As another example, chemical sensors can be used in asset monitoring systems to monitor the status or condition of assets in an industrial facility or other environment. As yet another example, chemical sensors can be used to protect people against toxic gases and other hazardous or dangerous chemicals, such as carbon dioxide ($CO_2$), ammonia ($NH_3$), hydrogen sulfide ($H_2S$), hydrogen gas ($H_2$), or volatile organic compounds (VOCs) and odors.

Chemical sensors routinely include one or more sensing layers, which have properties that vary based on the presence or concentration of one or more chemicals. These varying properties can be used to detect the presence of a chemical or to measure the concentration of a chemical. Sensing layers are often formed from organic compounds that interact in a reversible way with a chemical to be detected or measured. Sensing layers can also be formed using nano-composite materials that contain a host polymer and different functionalized forms of carbon nanotubes.

SUMMARY

This disclosure provides a method for chemical sensor fabrication and related sensor.

In a first embodiment, a method includes forming a hole in a first wafer and forming a sensor structure in or on a second wafer. The second wafer includes a piezoelectric material. The method also includes bonding the first wafer and the second wafer, where the sensor structure is located between the wafers. In addition, the method includes forming a sensing layer by depositing material between the wafers through the hole in the first wafer.

In particular embodiments, forming the sensing layer includes depositing a sensing layer material on the second wafer using direct printing. Also, in particular embodiments, forming the hole through the first wafer includes using ultrasonic milling, micro-drilling, laser drilling, wet etching, and/or plasma etching.

In other particular embodiments, bonding the first wafer and the second wafer includes depositing a spacer material on the first wafer around the hole and pressing the wafers so that the spacer material contacts both wafers. The spacer material could include frit glass paste that is cured into frit glass, where the frit glass has a thermal coefficient of expansion at least approximately equal to average thermal coefficients of expansion for the first and second wafers. The spacer material could also include an organic adhesive. In addition, the method may further include performing thermo-compression to bond the wafers.

In yet other particular embodiments, the method also includes forming multiple trenches in the first wafer, where the first wafer has multiple locally thinned areas associated with the trenches. The method further includes removing a portion of the first wafer by cutting the locally thinned areas of the first wafer.

In still other particular embodiments, multiple sensor structures are formed on the second wafer, where the multiple sensor structures include multiple bonding pads. Also, removing the portion of the first wafer exposes portions of at least some of the bonding pads. In addition, the method further includes forming conductive bumps on the exposed bonding pads.

In additional particular embodiments, the first wafer includes glass, and the second wafer includes quartz.

In a second embodiment, a sensor includes a piezoelectric substrate and at least one sensor structure formed in or on the substrate. The sensor also includes at least one bonding pad electrically coupled to the at least one sensor structure. The sensor further includes a cover separated from the substrate by a spacer, where the at least one sensor structure is located between the cover and the substrate and the cover has a hole. In addition, the sensor includes a sensing layer deposited between the cover and the substrate through the hole in the first wafer.

In a third embodiment, a system includes a printed circuit board and a sensor mounted on the printed circuit board. The sensor includes a piezoelectric substrate and at least one sensor structure formed in or on the substrate. The sensor also includes multiple bonding pads electrically coupled to the at least one sensor structure and a conductive bump on each of the bonding pads, where the conductive bumps are in electrical contact with the printed circuit board. The sensor further includes a cover separated from the substrate by a spacer, where the at least one sensor structure is located between the cover and the substrate and the cover has a hole. In addition, the sensor includes a sensing layer deposited between the cover and the substrate through the hole in the first wafer.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawings, in which.

DETAILED DESCRIPTION

FIGS. 1 through 5, discussed below, and the various embodiments used to describe the principles of the present invention in this patent document are by way of illustration only and should not be construed in any way to limit the scope of the invention. Those skilled in the art will understand that the principles of the invention may be implemented in any type of suitably arranged device or system.

Figure 1:
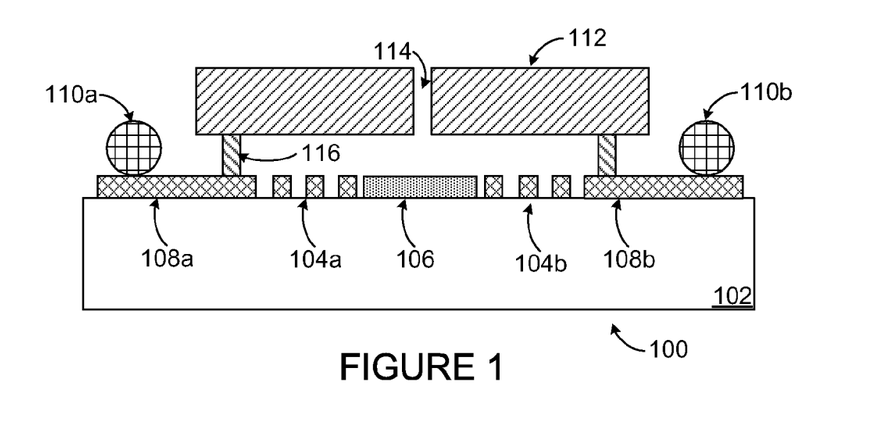
FIG. 1 illustrates an example chemical sensor according to this disclosure.

FIG. 1 illustrates an example chemical sensor 100 according to this disclosure. The embodiment of the chemical sensor 100 shown in FIG. 1 is for illustration only. Other embodiments of the chemical sensor 100 could be used without departing from the scope of this disclosure.

In general, the chemical sensor 100 can be used to detect the presence and/or concentration of one or more chemicals. In this document, the term "chemical" refers to any suitable substance being detected or measured, whether in the form of a chemical element or a simple or complex chemical compound. Also, the detection or measurement of a chemical can take various forms depending on the implementation. For example, the chemical sensor 100 could be used to detect the presence of a chemical, such as when the sensor 100 is used to detect whether a particular chemical is present at all or is present in at least a threshold amount or concentration. The chemical sensor 100 could also be used to measure a chemical, such as when the sensor 100 is used to measure the amount or concentration of the chemical.

As shown in FIG. 1, the chemical sensor 100 includes a substrate 102. The substrate 102 generally represents any suitable piezoelectric structure on which other components of the sensor 100 are formed or carried. The substrate 102 could, for example, represent a piezoelectric substrate such as quartz.

In this example embodiment, the sensor 100 represents a surface acoustic wave (SAW) Rayleigh sensor formed using two interdigital transducers (IDTs) 104a-104b, which may represent a SAW delay line. Each of the interdigital transducers 104a-104b includes two sets of conductive fingers (where one set of conductive fingers is interleaved with the other set of conductive fingers). The interdigital transducer 104a could be viewed as the input transducer, and the interdigital transducer 104b could be viewed as the output transducer. During operation, the interdigital transducer 104a produces acoustic waves based on an alternating input electrical signal. The acoustic waves propagate through the sensor 100 to the interdigital transducer 104b, which produces an output electrical signal based on the acoustic waves. Each of the interdigital transducers 104a-104b could be formed using any suitable material(s) with high electrical conductivity, such as highly-doped polysilicon or metal. Each of the interdigital transducers 104a-104b could also be formed in any suitable manner, such as by etching the polysilicon or metal using a mask. In addition, each of the interdigital transducers 104a-104b could include any number of conductive fingers, depending (among other things) on the designed bandwidth and operational frequency of the interdigital transducers. In addition, those skilled in the art will understand that other types of SAW devices could also be used, such as shared horizontal (SH)-Love SAW delay lines that include a silicon dioxide ($SiO_2$) or other guiding layer (not shown here).

A sensing layer 106 is located over the substrate 102 and between the interdigital transducers 104a-104b. The sensing layer 106 is generally exposed to the environment and is sensitive to one or more chemicals being detected or measured. The presence or level of a chemical being detected or measured typically alters one or more properties of the sensing layer 106. This affects the transport of the acoustic waves between the interdigital transducers 104a-104b, which can be determined by an external component (such as an external control electric circuit) and used to detect or measure the chemical. In this way, the sensing layer 106 provides a mechanism for identifying the presence or level of at least one chemical. The sensing layer 106 could be formed from any suitable material(s) depending, for example, on the chemical(s) to be detected or measured. For instance, poly-ethylene imine (PEI) functionalized with amino carbon nanotubes (CNTs) can be used for carbon dioxide sensing.

Two bonding pads 108a-108b are electrically coupled to the interdigital transducers 104a-104b. The bonding pads 108a-108b represent areas where conductive bumps 110a-110b can be formed in the sensor 100. The conductive bumps 110a-110b allow the sensor 100 to be electrically coupled to an external component, such as an antenna or electrical signal line. The bonding pads 108a-108b and the conductive bumps 110a-110b could be formed using any suitable material(s), such as aluminum bonding pads and gold conductive bumps. The bonding pads 108a-108b and the conductive bumps 110a-110b could also be formed in any suitable manner, such as by etching aluminum using a mask to form the bonding pads and by depositing gold stud bumps starting from gold wires to form the conductive bumps.

A cover 112 is placed over the interdigital transducers 104a-104b and the sensing layer 106. The cover 112 generally protects the interdigital transducers 104a-104b and the sensing layer 106. The cover 112 also includes an opening 114, through which the sensing layer 106 can be exposed to the ambient environment (and any chemicals in the ambient environment). The cover 112 is spaced apart from the interdigital transducers 104a-104b and the sensing layer 106 using one or more spacers 116, which in this example are formed over the bonding pads 108a-108b (although the spacers 116 could be formed in other areas, such as over the substrate 102 next to the bonding pads). The cover 112 and the one or more spacers 116 could be formed using any suitable material(s), such as a glass or quartz for cover fabrication and frit glass for spacer fabrication. The cover 112 and the one or more spacers 116 could also be formed in any suitable manner, such as by grinding glass or quartz to form the cover and screen printing or direct printing frit glass paste to form the spacers. In some embodiments, the spacers 116 have a thermal coefficient of expansion (TCE) that equals or approximates the TCE of a glass cover 112 or that approximates the average TCE of a piezoelectric cover 112 (in two perpendicular directions due to their anisotropic material properties) and that equals or approximates the average TCE of the piezoelectric substrate 102 (in two perpendicular directions). As a particular example, the spacers 116 can be formed from frit glass, and the TCE of the frit glass can be established during frit glass paste formulation.

In particular embodiments, acoustic waves produced by exciting the input interdigital transducer 104a can propagate through the surface of the substrate 102 to the output interdigital transducer 104b. The propagation velocity of the acoustic waves at the surface of the piezoelectric substrate 102 (for Rayleigh SAW devices) or through a guiding layer (for SH-Love SAW devices) may depend on the properties of the sensing layer 106. At least one chemical to be detected or measured affects one or more properties of the sensing layer 106 (such as its mass loading, electrical, and visco-elastic properties). As a result, changes in the propagation velocity of the acoustic waves can be directly related to variations in that chemical, and propagation velocity changes in the sensor 100 can be monitored and used to determine the presence or concentration of the chemical.

Depending on its composition, the sensing layer 106 often needs to be thermally consolidated and operated at lower temperatures. For example, the sensing layer 106 could have a maximum temperature of 250° C. or even 60° C. As a result, constraints are often necessary during formation of the chemical sensor 100. As described in more detail below, the sensing layer 106 can be formed after a packaging process has been performed (which includes coupling the cover 112 to the substrate 102 using the spacers 116). Among other things, this may help to preserve the functionality of the organic or other sensing layer 106.

Although FIG. 1 illustrates one example of a chemical sensor 100, various changes may be made to FIG. 1. For example, the layout and arrangement of components in the chemical sensor 100 could be altered according to particular needs. Also, the sizes, shapes, and relative positions of the components in the chemical sensor 100 are for illustration only. In addition, FIG. 1 illustrates the chemical sensor 100 as a SAW Rayleigh sensor, other types of sensors (such as SAW shared horizontal and bulk acoustic wave sensors) could be used. These other types of sensors could be formed as described below, where the sensors are packaged and then the sensing layers are formed after packaging.

FIGS. 2A through 2H illustrate an example technique for forming chemical sensors according to this disclosure. The technique shown in FIGS. 2A through 2H is for illustration only. Other techniques could be used to fabricate one or more chemical sensors without departing from the scope of this disclosure. Also, for ease of illustration and explanation, the technique shown in FIGS. 2A through 2H is described with respect to the chemical sensor 100 of FIG. 1. The technique shown in FIGS. 2A through 2H could be used to form any suitable sensor, and the chemical sensor 100 of FIG. 1 could be formed using any suitable technique.

The chemical sensors fabricated using this technique (such as multiple sensors 100 formed on the same wafer) may operate based on the piezoelectric effect, so the sensors may be sensitive to strain developed by their package. As a result, low stress precautions can be taken during fabrication and packaging of the sensors. For example, the use of metal covers can be eliminated (although metal covers could still be used depending on particular implementations). Also, mismatches between the TCE of different components can be reduced or eliminated. Further, whenever possible, the packaging materials can be designed to avoid mechanical stresses of thermal origins. In addition, the chemical sensors fabricated using this technique may use sensing layers 106 that are sensitive to high temperature extremes. In this technique, the sensing layers 106 in the chemical sensors 100 can be formed after various operations have been performed to package the sensors 100. As a result, the sensing layers 106 may not be exposed to the elevated temperatures used to package the sensors 100, helping to reduce or eliminate damage to the sensing layers 106.

Figure 2A:
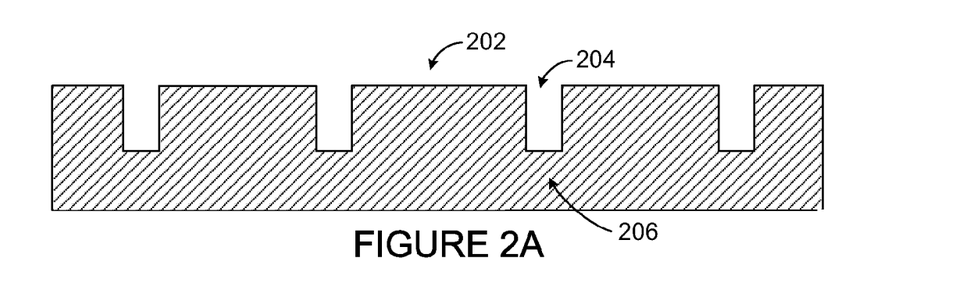
FIGS. 2A through 2H illustrate an example technique for forming chemical sensors according to this disclosure.

As shown in FIG. 2A, a cover wafer 202 is etched to form multiple trenches 204. The cover wafer 202 represents a wafer of material that is used to form the covers 112 for multiple sensors 100 made simultaneously on the same sensor wafer (which is used to form the substrates 102 of multiple sensors 100). The cover wafer 202 could be formed from any suitable material(s), such as a circular quartz or glass wafer. In particular embodiments, the cover wafer 202 can be selected to have the same diameter and thickness as the sensor wafer. The cover wafer 202 could also have the same or similar TCE as the material(s) used to form the spacers 116 in the sensors 100. Further, the cover wafer 202 could be etched in any suitable manner, such as by sawing the trenches 204 across the cover wafer 202 using a cutting disc. In addition, the trenches 204 could have any suitable width, depth, and spacing, such as a depth of 50-100 µm, while the width of the trench can be based on the width of the cutting disc. The formation of the trenches 204 in the cover wafer 202 leads to the creation of locally thinned areas 206 of the cover wafer 202. These locally thinned areas 206 are located below the trenches 204 in FIG. 2A, and these areas 206 have a thickness less than the thickness of the non-etched areas of the cover wafer 204.

Figure 2B:
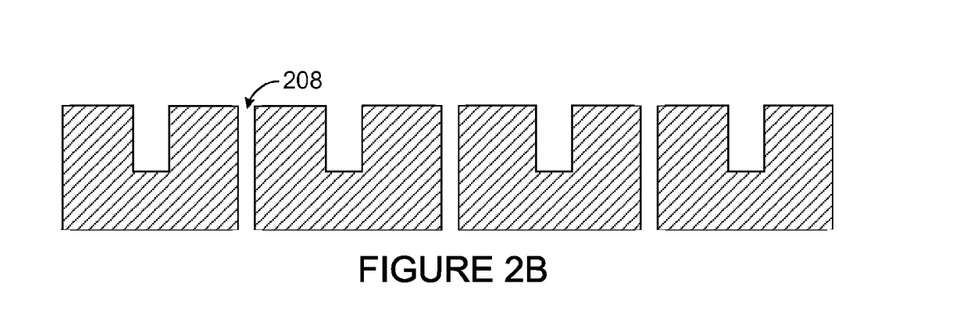

As shown in FIG. 2B, the cover wafer 202 is perforated by forming holes 208 in the cover wafer 202. The holes 208 could have any suitable size and shape, and the sizes and shapes need not be consistent. Any suitable technique(s) could be used to form the holes 208 in the cover wafer 202.

Example techniques may include ultrasonic milling, microdrilling, laser drilling, wet etching, and plasma etching.

Figure 2C:
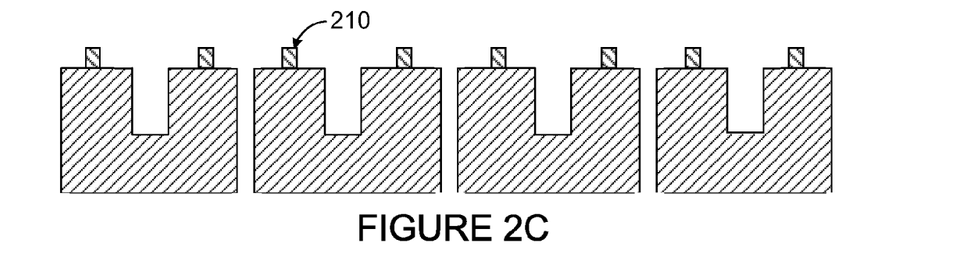

As shown in FIG. 2C, spacer material 210 is deposited on the cover wafer 202. The spacer material 210 is used to form the spacers 116 in the sensors 100. The spacer material 210 could represent any suitable material(s), such as frit glass paste having a TCE that matches or approximates the average TCE of the cover wafer 202 and the average TCE of the sensor wafer. In some embodiments, the frit glass paste is formulated to have a firing temperature below the Curie temperature of quartz. As another example, the spacer material 210 could represent an organic adhesive such as benzo-cyclo-butene (BCB). Any other or additional adhesive material(s) or other material(s) could be used.

The spacer material 210 can be deposited on the cover wafer 202 in any suitable manner, such as by screen printing or direct printing. The deposition of the spacer material 210 by direct printing could represent a selective, maskless deposition of a liquid phase of the spacer material. In addition, the spacer material 210 can be deposited to any suitable height, such as 15-50 µm. A partial or complete drying of the spacer material 210 can then occur, which may help the spacer material 210 to retain its position on the cover wafer 202 during subsequent process steps.

Figure 2D:
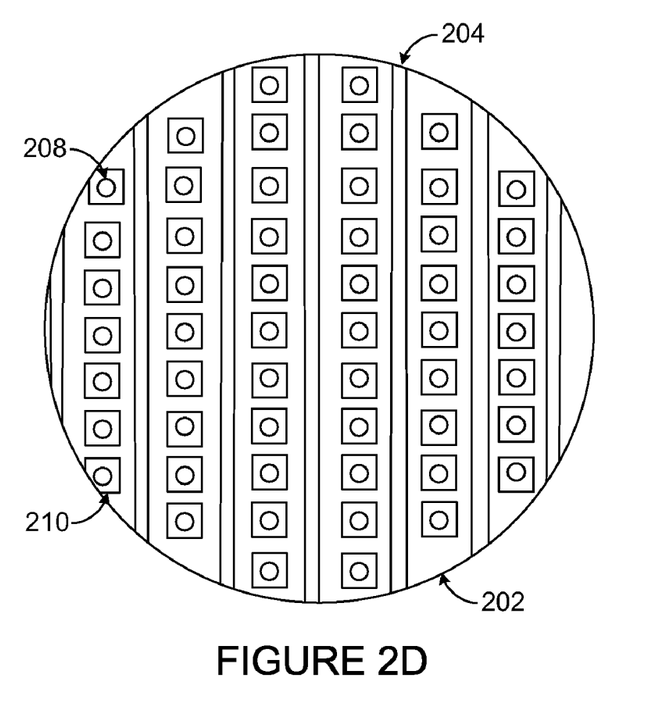

At this point, the cover wafer 202 may appear as shown in FIG. 2D. Here, the cover wafer 202 includes the trenches 204 extending across the cover wafer 202. Also, the holes 208 have been formed in the areas between the trenches 204, and the spacer material 210 has been deposited around each of the holes 208. It may be noted that the shapes, sizes, and arrangements of the components in FIG. 2D are for illustration only. The trenches 204, the holes 208, the spacer material 210, and even the cover wafer 202 could have any other suitable size or shape, and the components on the cover wafer 202 could have any suitable arrangement.

Figure 2E:
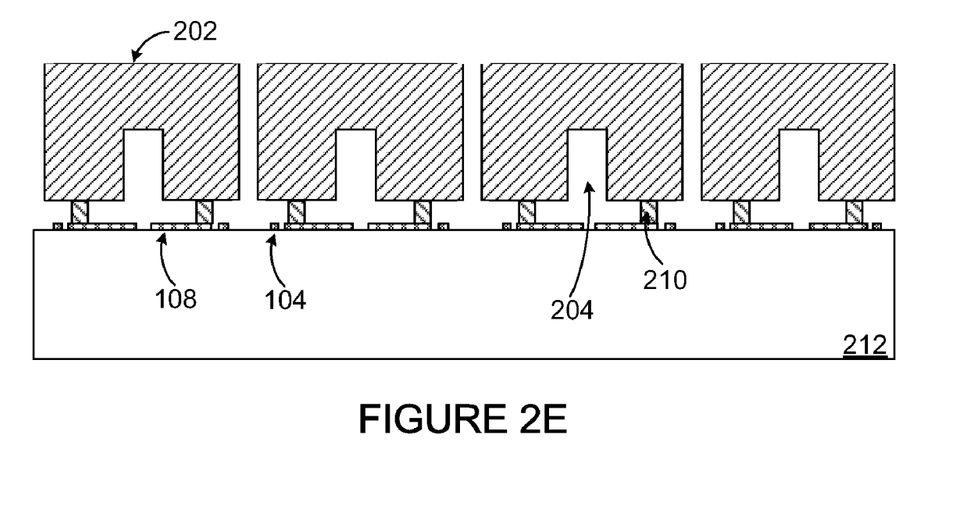

As shown in FIG. 2E, a sensor wafer 212 is processed to form the various interdigital transducers 104 and bonding pads 108 for multiple sensors 100. The sensor wafer 212 could be formed using any suitable material(s), such as a circular quartz wafer. Also, as shown in FIG. 2E, the cover wafer 202 is aligned with and bonded to the sensor wafer 212. This may include ensuring that the spacer material 210 is properly aligned with the bonding pads 108 on the surface of the sensor wafer 212 (although the spacer material 210 could also contact the sensor wafer 212). During alignment, the trenches 204 in the cover wafer 202 are positioned to overlap portions of the bonding pads 108 on the sensor wafer 212.

Once aligned properly, the wafers 202 and 212 undergo a bonding treatment, such as thermo-compression treatment, to bond the wafers together via the spacer material 210. For example, when the spacer material 210 represents frit glass paste, the wafers can undergo firing (such as at temperatures below 400° C.) to cure the frit glass paste into frit glass. The frit glass paste can be fired so that solid frit glass frames surround at least a portion of each sensor 100 on the sensor wafer 212 (such as by surrounding the interdigital transducers 104a-104b of the sensors 100). In particular embodiments, firing of frit glass paste can occur with oxygen in the ambient environment, and pure and dry nitrogen or a high vacuum can be used as the ambient environment during alignment and thermal consolidation of the frit glass paste. The firing may take place during frit glass paste consolidation on the cover wafer 202 before final alignment and bonding in nitrogen or a vacuum. When BCB adhesive is used as the spacer material 210, thermal treatment in the range of 250° C. can be used to cure the adhesive.

Figure 2F:
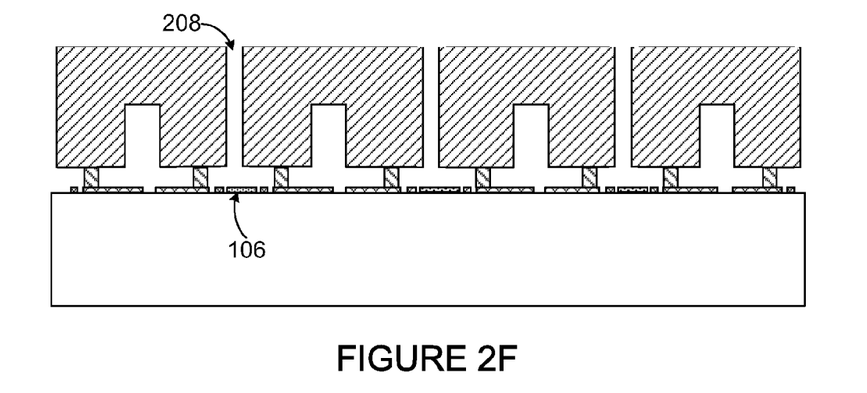

As shown in FIG. 2F, after the wafers are bonded together, the sensing layers 106 are formed for the sensors 100. In this example, the sensing layers 106 are formed by depositing sensing layer material(s) onto the sensor wafer 212 through the holes 208 in the cover wafer 202. The sensing layer material(s) can be deposited in any suitable manner, such as by depositing functionalized organic material in a liquid phase using a direct printing tool.

Figure 2G:
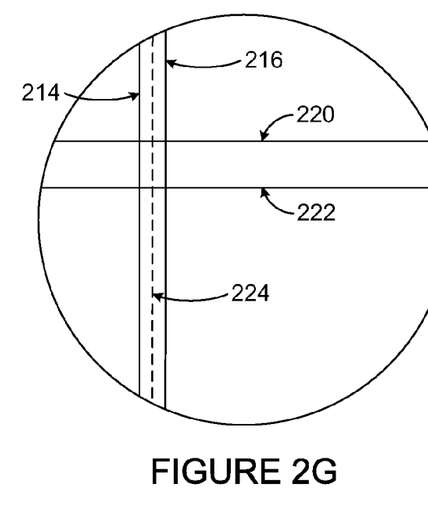
Figure 2H:
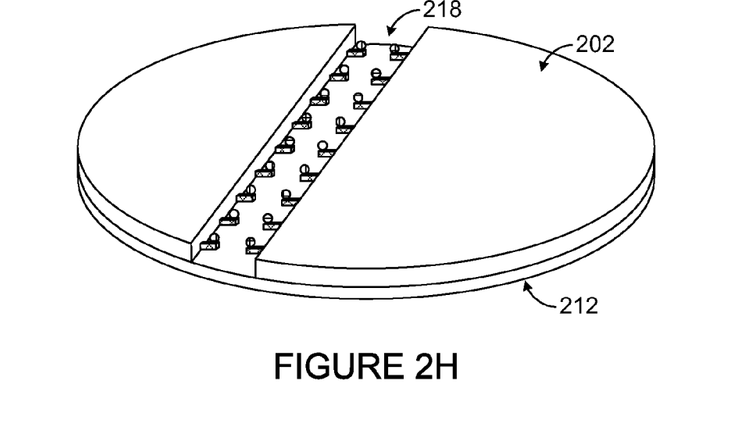

As shown in FIGS. 2G and 2H, a cutting sequence can be used to expose the sensors' bonding pads for application of conductive bumps and to "dice" or separate the sensors from one another. For example, the bonded wafers can be placed on a plastic foil support or other support, and one or both wafers can be sawed using a rotating disc. In this example, cuts 214-216 can be made in the cover wafer 202 to remove a single strip 218 of the cover wafer 202 between multiple sensors 100 being formed. These two cuts could be designed to saw completely through locally thinned areas 206 of the cover wafer 202, which means the cuts can be designed to be less deep (since the locally thinned areas 206 are located over trenches 204 that have already been formed in the cover wafer 202). In this way, the cuts 214-216 would not cut into the sensor wafer 212 or the bonding pads 108 on the surface of the sensor wafer 212. The same two cuts can be repeated to remove multiple strips 218 of the cover wafer 202. At this point, a bumping process could occur to place gold or other conductive bumps on the exposed bonding pads.

After that, additional cuts to the wafers may occur in order to separate the sensors 100 being formed. For example, cuts 220-222 are used to saw through the cover wafer 202 and partially into the sensor wafer 212, and cut 224 is used to saw partially into the sensor wafer 212 below a removed strip 218 of the cover wafer 202. These cuts can be repeated as necessary to partially cut the sensor wafer 212 between each sensor 100 being formed. Once the cuts are completed, the sensors 100 can be completely separated from one another using a heavy rolling process, where a heavy mass is rolled over the bonded wafers to separate the sensors 100 along the partial cuts through the sensor wafer 212. At this point, the sensors 100 can be mounted on printed circuit boards, attached to wired connections or wireless antennas, or used in any other suitable manner.

Although FIGS. 2A through 2H illustrate one example of a technique for forming chemical sensors, various changes may be made to FIGS. 2A through 2H. For example, any other suitable techniques could be used to form the various structures of the chemical sensors 100, and the operations shown in FIGS. 2A through 2H could occur in a different order.

Figure 3:
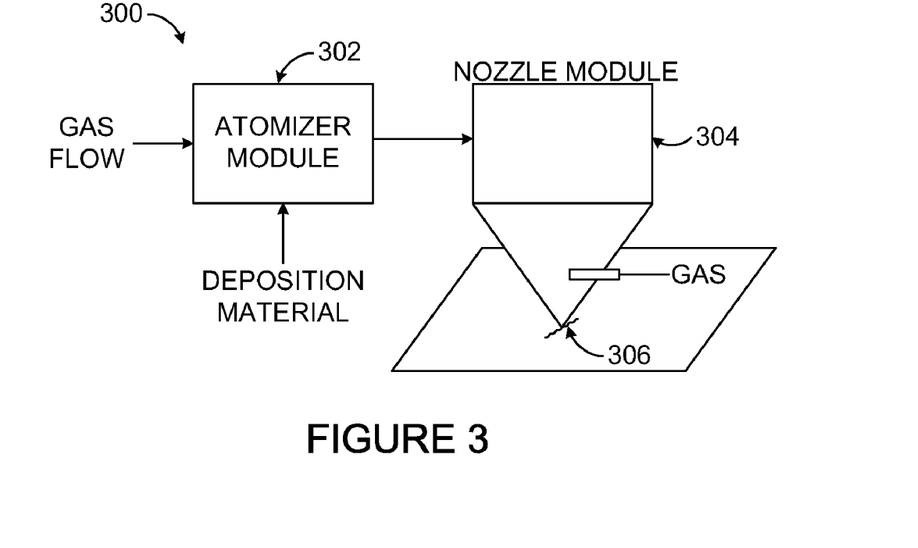
FIG. 3 illustrates an example printing system for additively depositing material on a wafer during chemical sensor formation according to this disclosure.

FIG. 3 illustrates an example printing system 300 for additively depositing material on a wafer during chemical sensor formation according to this disclosure. The embodiment of the printing system 300 shown in FIG. 3 is for illustration only. Other embodiments of the printing system 300 could be used without departing from the scope of this disclosure.

In this example, the printing system 300 represents a direct printing system that can be used to deposit frit glass paste, BCB adhesive, sensing layer material, or other liquid phase deposition material onto a cover wafer, sensor wafer, or other structure without using a mask. As shown here, the printing system 300 includes an atomizer module 302 and a nozzle module 304. The atomizer module 302 mixes at least one deposition material with a gas flow, producing atomized liquid phase deposition material that is provided to the nozzle module 304. The nozzle module 304 then removes the gas from the atomized deposition material and deposits the deposition material onto a cover wafer, sensor wafer, or other structure. In this example, the deposition material is deposited as a liquid line 306 on a wafer or other structure.

The use of a direct printing system to deposit frit glass paste, BCB adhesive, sensing layer material, or other material onto a wafer may be beneficial in several ways. For example, direct printing may require no masking steps to be performed. Also, direct printing may result in little or no material being lost during the printing process.

In particular embodiments, the printing system 300 can be used to form the sensing layers 106 in the chemical sensors 100 as follows. The printing system 300 can be programmed with the trajectory of the dispenser tip (the tip of the nozzle module 304 where the deposition material leaves the nozzle module 304). The trajectory can be selected so that the liquid phase of the sensing layer material is finely dropped only in selected areas. The printing system 300 can be filled or otherwise supplied with the liquid phase material to be dispensed, and the liquid phase material is dispensed in the selected areas. At this point, consolidation of the material into the sensing layers 106 may occur, such as by thermal treatment of the bonded wafers after material deposition. An annealing temperature used during the thermal treatment may depend, among other things, on the chemical composition of the sensing layers 106.

Although FIG. 3 illustrates one example of a printing system 300 for additively depositing material on a wafer during chemical sensor formation, various changes may be made to FIG. 3. For example, other techniques besides direct printing could be used to selectively deposit material onto a wafer.

Figure 4:
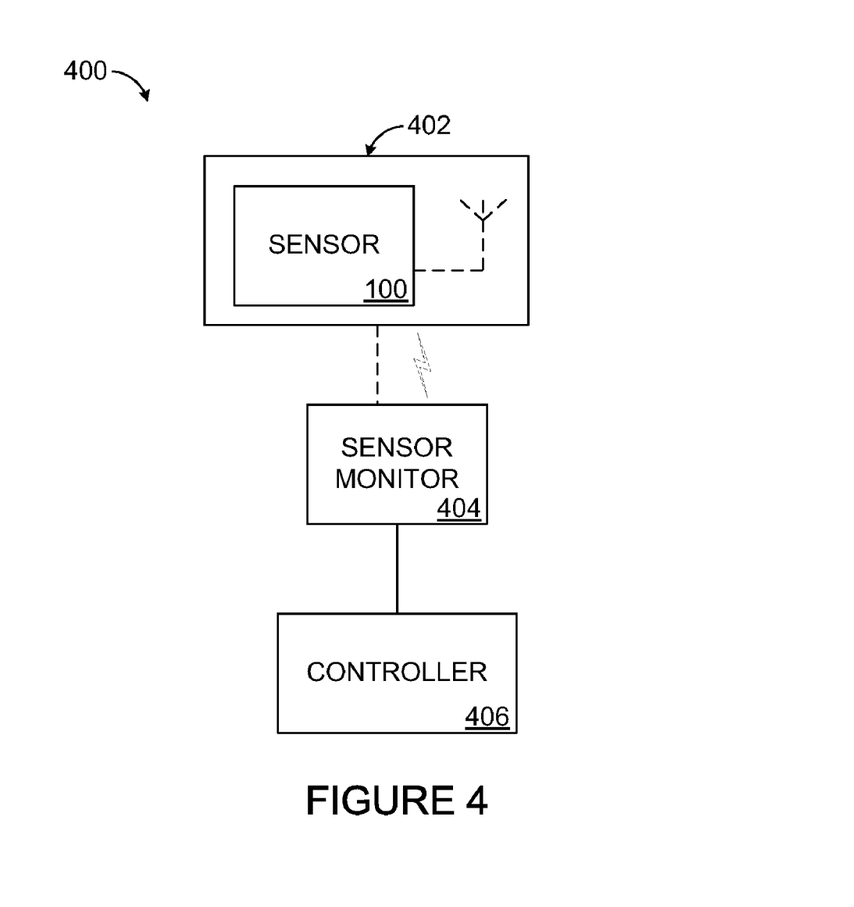
FIG. 4 illustrates an example system using one or more chemical sensors according to this disclosure.

FIG. 4 illustrates an example system 400 using one or more chemical sensors according to this disclosure. The embodiment of the system 400 shown in FIG. 4 is for illustration only. Other embodiments of the system 400 could be used without departing from the scope of this disclosure. Also, for ease of illustration and explanation, the system 400 of FIG. 4 is described with respect to the chemical sensor 100 of FIG. 1. The chemical sensor 100 of FIG. 1 could be used with any suitable system or device.

In this example, the system 400 includes at least one chemical sensor 100 that has been mounted on a printed circuit board 402. The printed circuit board 402 generally represents a structure on which the sensor 100 and other circuitry can be mounted or formed. The other circuitry could include an antenna, such as a loop antenna formed on or around a small printed circuit board. The antenna allows for wireless transmissions from the sensor 100, although wired connections could also be used to communicate with the sensor 100. The conductive bumps 110a-110b of the sensor 100 may allow the sensor 100 to be "flip chip" mounted to pads of the printed circuit board 402. The printed circuit board 402 includes any suitable circuit-carrying substrate. Additional details regarding the attachment of a sensor to an antenna (as wells as details regarding sensors in general) can be found in U.S. patent application Ser. No. 11/286,064 and U.S. patent application Ser. No. 11/331,722, both of which are hereby incorporated by reference.

The sensor 100 is in wired and/or wireless communication with a sensor monitor 404. The sensor monitor 404 uses the sensor 100 to detect or measure one or more chemicals. As a particular example, a change in the concentration of a chemical may alter the properties of the sensing layer 106 in the sensor 100, which may change the signals transmitted by the sensor 100. As a result, the sensor monitor 404 can use the signals from the sensor 100 to detect or measure the concentration of the chemical. The sensor monitor 404 could also process this information further (such as by determining if a threshold level of the chemical has been reached and triggering an output if so), or the sensor monitor 404 could output the data to a controller 406 for further analysis. The sensor monitor 404 includes any suitable structure for using electrical signals from one or more sensors, such as to extract information or to detect or identify one or more conditions.

The controller 406 controls at least one process, device, or portion thereof based on outputs of the sensor monitor 404. For example, the controller 406 could receive an indication from the sensor monitor 404 that a concentration or amount of a chemical has been detected or has exceeded a threshold. The controller 406 could also receive measurement data from the sensor monitor 404 and determine itself that a concentration or amount of a chemical has been detected or has exceeded a threshold. The controller 406 could then take any suitable action. For instance, if the chemical is carbon dioxide or other dangerous or hazardous chemical, the controller 406 could trigger an alarm or initiate venting of a particular area. The controller 406 could also make adjustments to a process in an industrial facility based on the sensor data. The controller 406 includes any hardware, software, firmware, or combination thereof for controlling at least one device, process, or portion thereof based on data from one or more sensors.

Each of the connections between components in FIG. 4 could represent any suitable wired or wireless connection. For example, the sensor 100 could be in wired or wireless communication with the sensor monitor 404, and the sensor monitor 404 could be wired to the controller 406. However, any suitable type of connection could be used between components.

Although FIG. 4 illustrates one example of a system 400 using one or more chemical sensors, various changes may be made to FIG. 4. For example, a chemical sensor may communicate with any number of monitors, and each monitor could communicate with any number of chemical sensors. Also, any number of monitors could communicate with any number of controllers. In addition, the functional division shown in FIG. 4 is for illustration only. Various components in FIG. 4 could be combined, subdivided, or omitted and additional components could be added according to particular needs. As a specific example, some or all of the functionality of the sensor monitor could be incorporated into the controller or vice versa.

Figure 5:
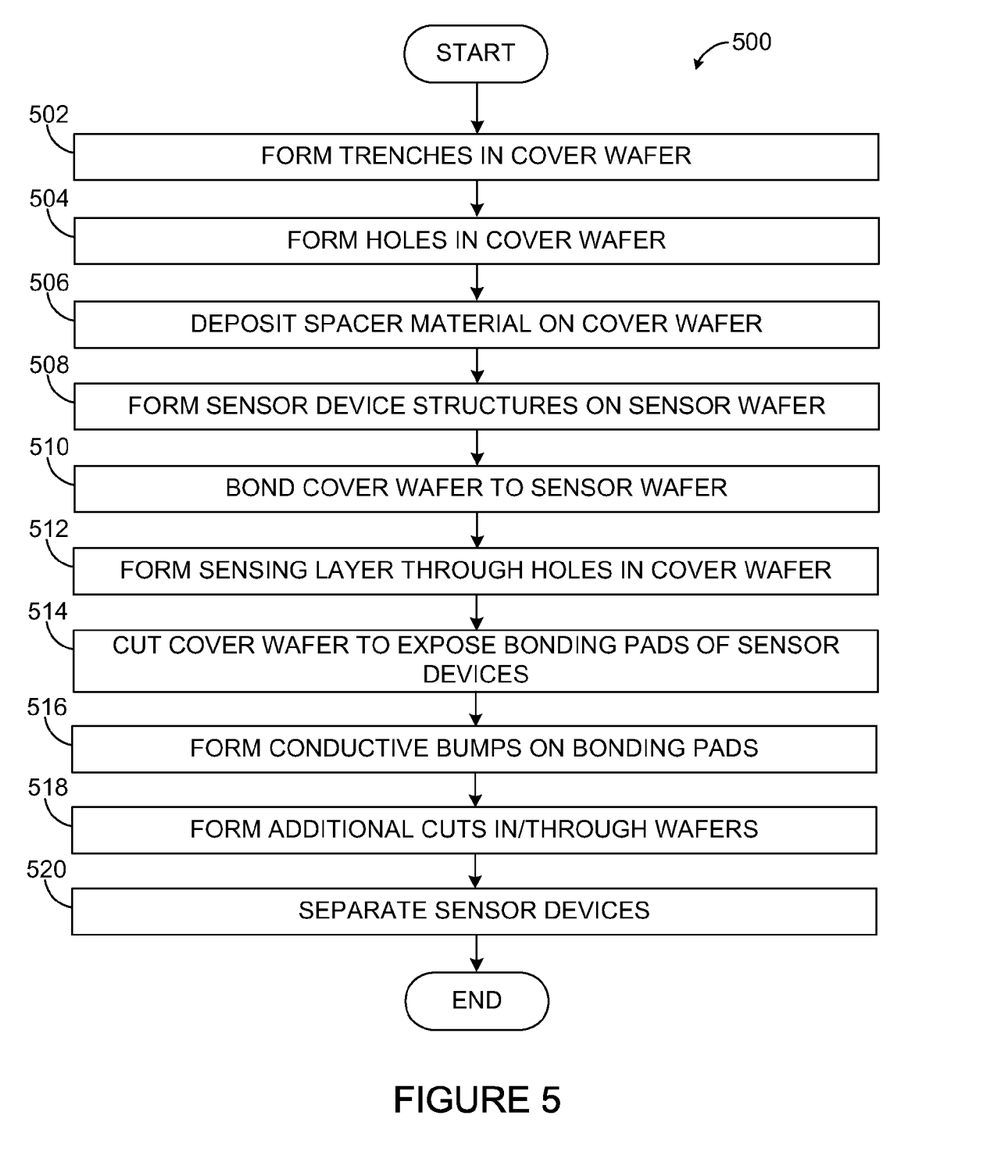
FIG. 5 illustrates an example method for forming packaged chemical sensors according to this disclosure.

FIG. 5 illustrates an example method 500 for forming packaged chemical sensors according to this disclosure. The embodiment of the method 500 shown in FIG. 5 is for illustration only. Other embodiments of the method 500 could be used without departing from the scope of this disclosure.

One or more trenches are formed in a cover wafer at step 502. This could include, for example, forming multiple trenches 204 in a glass or quartz cover wafer 202. The trenches 204 could be 50-100 µm deep and be formed by sawing with a cutting disc. One or more holes are formed in the cover wafer at step 504. This may include, for example, forming multiple holes 208 in the cover wafer 202 using ultrasonic milling, micro-drilling, laser drilling, wet etching, or plasma etching. Spacer material is deposited on the cover wafer at step 506. This could include, for example, depositing frit glass paste or BCB adhesive on the cover wafer 202 using direct or screen printing.

One or more sensor device structures are formed on a sensor wafer at step 508. This could include, for example, forming one or more interdigital transducers and bonding pads on the sensor wafer 212. The interdigital transducers and bonding pads could be formed by depositing and etching conductive materials. The cover wafer and the sensor wafer are bonded at step 510. This could include, for example, aligning the trenches 204 and the frit glass paste, BCB, or other spacer material 210 on the cover wafer 202 with the interdigital transducers 104 and their bonding pads 108 on the sensor wafer 212. Any other suitable technique could be used to align the wafers. This may also include pressing the wafers together and curing the spacer material 210, such as by annealing the frit glass paste to harden the frit glass paste.

A sensing layer is formed in each of the sensors at step 512. This may include, for example, depositing one or more sensing layer materials onto the sensor wafer 212 through the holes 208 in the cover wafer 202. The sensing layer materials can be deposited in any suitable manner, such as by using direct printing.

The cover wafer is cut to expose the bonding pads of the sensor devices at step 514. This could include, for example, performing two cuts between columns of sensor devices using a sawing disc, where each cut travels completely through locally thinned areas 206 of the cover wafer 202. In other words, these cuts may occur over areas where the trenches 204 were formed in the cover wafer 202. As a result, these cuts may allow strips 218 of the cover wafer 202 to be completely removed without the sawing disc approaching too close to the sensor devices. Conductive bumps are formed on the exposed bonding pads at step 516. This may include, for example, gold wire bonding on the bonding pads 108a-108b of the sensor 100 (such as by thermo-compression of the wire on the bonding pads), followed by wire cutting to produce the final gold stud bump on each bonding pad.

Additional cuts are formed in or through the bonded wafers at step 518. This may include, for example, performing cuts between rows of sensor devices using a sawing disc. These cuts may travel completely through the cover wafer 202 and partially through the sensor wafer 212. This may also include performing cuts between columns of sensor devices through the strips 218 of the cover wafer 202 that have been removed. Again, these cuts may travel partially through the sensor wafer 212. At this point, the sensor wafer 212 has been partially cut between each of the sensor devices, and the sensor devices are separated at step 520. This may include, for example, rolling a heavy mass over the bonded wafers to cause the sensors 100 to separate from one another.

Although FIG. 5 illustrates one example of a method 500 for forming multiple packaged chemical sensors, various changes may be made to FIG. 5. For example, while shown as a series of steps, various steps in FIG. 5 could overlap, occur in parallel, occur in a different order, or occur multiple times. As a particular example, formation of the sensor devices on the sensor wafer could occur before or during formation of the cover wafer.

It may be advantageous to set forth definitions of certain words and phrases used throughout this patent document. The term "couple" and its derivatives refer to any direct or indirect communication between two or more elements, whether or not those elements are in physical contact with one another. The terms "over," "above," "below," and the like denote relative positions of two or more elements in a particular orientation and do not require direct contact between the elements. The terms "include" and "comprise," as well as derivatives thereof, mean inclusion without limitation. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like. The term "controller" means any device, system, or part thereof that controls at least one operation. A controller may be implemented in hardware, firmware, software, or some combination of at least two of the same. The functionality associated with any particular controller may be centralized or distributed, whether locally or remotely.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A method of forming a sensor comprising:
   forming a hole through a first wafer;
   forming a sensor structure over a second wafer, the second wafer comprising a piezoelectric material;
   bonding the first wafer and the second wafer, wherein the sensor structure is located between the wafers;
   forming a sensing layer by depositing a sensing layer material between the bonded wafers through the hole of the first wafer, the sensing layer having a property that varies based upon a presence or concentration of a chemical to be measured using the sensor;
   forming multiple trenches in the first wafer, the first wafer having multiple locally thinned areas associated with the trenches; and
   removing a portion of the first wafer by cutting the locally thinned areas of the first wafer.

2. The method of claim 1, wherein forming the sensing layer comprises depositing the sensing layer material over the second wafer using direct printing.

3. The method of claim 1, wherein forming the hole through the first wafer comprises using at least one of: ultrasonic milling, micro-drilling, laser drilling, wet etching, and plasma etching.

4. The method of claim 1, wherein bonding the first wafer and the second wafer comprises:
   depositing a spacer material over the first wafer around the hole; and
   pressing the wafers so that the spacer material contacts both wafers.

5. The method of claim 4, wherein the spacer material comprises frit glass paste that is cured into frit glass, the frit glass having a thermal coefficient of expansion at least approximately equal to average thermal coefficients of expansion for the first and second wafers.

6. The method of claim 4, wherein the spacer material comprises an organic adhesive.

7. The method of claim 4, further comprising performing thermo-compression to bond the wafers.

8. The method of claim 1, wherein:
   multiple sensor structures are formed over the second wafer, the multiple sensor structures comprising multiple bonding pads;
   removing the portion of the first wafer exposes portions of at least some of the bonding pads; and
   further comprising forming conductive bumps over the exposed bonding pads.

9. The method of claim 1, wherein:
   the first wafer comprises glass; and
   the second wafer comprises quartz.

10. The method of claim 1, wherein forming the sensing layer comprises depositing the sensing layer material between the bonded wafers such that a portion of the sensing layer material is physically located between the first and second wafers in a direction perpendicular to a top surface of one wafer and a bottom surface of another wafer.

11. A sensor comprising:
    a piezoelectric substrate;
    at least one sensor structure over the substrate;
    at least one bonding pad electrically coupled to the at least one sensor structure;
    a cover separated from the substrate by at least one spacer, the at least one sensor structure located between the cover and the substrate, the cover having a hole; and
    a sensing layer between the cover and the substrate;
    wherein the at least one spacer is located over the at least one bonding pad such that each bonding pad has a first portion within a space between the cover and the substrate and a second portion over the substrate but not under the cover.

12. The sensor of claim 11, wherein the sensing layer is deposited over the substrate using direct printing.

13. The sensor of claim 11, wherein the hole through the cover is formed using at least one of: ultrasonic milling, micro-drilling, laser drilling, wet etching, and plasma etching.

14. The sensor of claim 11, wherein the cover and the substrate are bonded together by the at least one spacer.

15. The sensor of claim 14, wherein the at least one spacer comprises at least one of: frit glass and an organic adhesive.

16. The sensor of claim 11, wherein:
    the cover comprises glass; and
    the substrate comprises quartz.

17. A system comprising:
    a printed circuit board; and
    a sensor mounted over the printed circuit board, the sensor comprising:
      a piezoelectric substrate;
      at least one sensor structure over the substrate;
      at least one bonding pad electrically coupled to the at least one sensor structure;
      at least one conductive bump over the at least one bonding pad and in electrical contact with the printed circuit board;
      a cover separated from the substrate by at least one spacer, the at least one sensor structure located between the cover and the substrate, the cover having a hole; and
      a sensing layer between the cover and the substrate;
      wherein the at least one spacer is located over the at least one bonding pad such that each bonding pad has a first portion within a space between the cover and the substrate and a second portion over the substrate but not under the cover.

18. The system of claim 17, wherein:
    the sensing layer is deposited over the substrate using direct printing; and
    the hole through the cover is formed using at least one of: ultrasonic milling, micro-drilling, laser drilling, wet etching, and plasma etching.

19. The system of claim 17, wherein the cover and the substrate are bonded together by the at least one spacer, the at least one spacer comprising at least one of: frit glass and an organic adhesive.

20. The system of claim 17, further comprising:
    a monitor configured to receive signals from the sensor; and
    a controller configured to analyze data associated with the signals received by the monitor.

* * * * *